US008164072B2

(12) United States Patent
Lihl et al.

(10) Patent No.: US 8,164,072 B2
(45) Date of Patent: Apr. 24, 2012

(54) DEVICE AND METHOD FOR PREPARING SPECIMENS

(75) Inventors: Reinhard Lihl, Vienna (AT); Guenter Resch, Vienna (AT)

(73) Assignee: Leica Mikrosysteme GmbH, Vienna (AT)

( * ) Notice: Subject to any disclaimer, the term of this patent is extended or adjusted under 35 U.S.C. 154(b) by 122 days.

(21) Appl. No.: 12/685,318

(22) Filed: Jan. 11, 2010

(65) Prior Publication Data

US 2010/0181495 A1    Jul. 22, 2010

(30) Foreign Application Priority Data

Jan. 22, 2009    (AT) .................. A 113/2009

(51) Int. Cl.
*G01N 1/30*    (2006.01)
*G01N 33/48*    (2006.01)
*B26B 1/00*    (2006.01)
*C12M 1/34*    (2006.01)

(52) U.S. Cl. ............. 250/443.1; 250/306; 250/440.11; 250/311

(58) Field of Classification Search .. 250/440.11–443.1, 250/306, 310–311
See application file for complete search history.

(56) References Cited

U.S. PATENT DOCUMENTS 6,484,564 B1 * 11/2002 Hayashida ................... 73/40
7,413,872 B2 * 8/2008 Frederik et al. .............. 435/67
2004/0157284 A1 * 8/2004 Frederik et al. ............ 435/40.5
2004/0231594 A1   11/2004 Edwards et al.

FOREIGN PATENT DOCUMENTS

WO    02/077612    10/2002

OTHER PUBLICATIONS

Trachtenberg, S.; A Fast-Freezing Device with a Retractable Environmental Chamber, Suitable for Kinetic Cyro-Electron Microscopy Studies; Journal of Structural Biology 123, 45-55 (1998), Article No. SB984015, Academic Press.

* cited by examiner

*Primary Examiner* — Jack I. Berman
*Assistant Examiner* — Wyatt Stoffa
(74) *Attorney, Agent, or Firm* — Schlee IP International, P.C.; Alexander R. Schlee

(57) ABSTRACT

A method and a device for preparing specimens for a cryo-electron microscope are described. A carrier is fixed to a holder, sample liquid is applied to the carrier, and a blotting device for removing excess sample liquid from the carrier by means of the absorbing medium is applied. The absorbing medium is illuminated with light and a change in the optical properties of the absorbing medium is detected by means of an optical sensor device. A control moves the blotting away from the carrier depending on a change in the detected optical properties.

16 Claims, 5 Drawing Sheets

DEVICE AND METHOD FOR PREPARING SPECIMENS

CROSS-REFERENCE TO RELATED APPLICATION

This application claims the priority of the Austrian patent application AT 113/2009 having a filing date of Jan. 22, 2009. The entire content of this prior Austrian patent application AT 113/2009 is herewith incorporated by reference.

BACKGROUND OF THE INVENTION

The invention relates to a device for preparing specimens for an electron microscope, preferably a cryo-electron microscope, comprising a holder for holding a carrier, a movable blotting device for absorbing excess sample liquid applied on the carrier by means of a substantially planar absorbing medium, a control that is adapted to move the blotting device towards the carrier, and an environmental chamber in which the holder and the blotting device are arranged.

Further, the invention relates to a method for preparing specimens for an electron microscope, preferably a cryo-electron microscope in which the above-mentioned device is used, the method comprising the following steps: mounting a carrier in a holder, the holder being located in an environmental chamber, applying a sample liquid on the carrier for wetting the surface of the carrier with sample liquid, removing the excess sample liquid present on the carrier by means of an absorbing medium arranged on a movable blotting device, and absorbing the sample liquid into the absorbing medium, the blotting device being moved towards the carrier by means of a control for absorbing the sample liquid by the absorbing medium, and moving the blotting device away from the carrier by means of the control after termination of the absorption of excess sample liquid.

The performance of electron microscopy, in particular of transmission electron microscopy, in the study of the ultrastructure of biological specimens is remarkable. For meaningful examinations, however, a previous, structure-maintaining preparation of the specimen is necessary due to the high vacuum present in the electron microscope and the high-energy electron beam. Common preparation techniques mostly include a fixing of the sample by means of chemical fixing agents and an extraction of the water. In addition, for increasing the contrast an artificial contrasting by introducing atoms having a high atomic number is performed, e.g. by means of uranyl acetate in negative contrasting. All these preparation steps can result in deformations of the object to be examined or to the formation of artefacts, and require a careful and critical image analysis.

Cryo-electron microscopy has proven to be particularly suitable for examinations of biological structures. Given this technology, an aqueous sample is cryofixed, i.e. it is cooled very fast while avoiding the formation of ice crystals. The objects to be examined, for example cells, enzymes, viruses or lipid layers, are thus embedded in a thin vitrified ice layer and microscopically examined in this state. Cryofixed samples withstand the high vacuum present in the electron microscope. The great advantage of cryofixing over the aforementioned fixing methods is that the biological structures can be preserved in their native state and can be examined in their physiological environment. The risk of a formation of artefacts is significantly lower than is the case in the chemical preparation methods. However, the contrast is likewise very little and the low signal-to-noise ratio requires a reproduction of the structure information by means of image processing.

Likewise disadvantageous is the higher sensitivity of the cryofixed samples to the electron beam. A contrasting is largely dispensed with due to the formation of artefacts, and the structure is digitally reconstructed.

Independent of the type of specimen preparation, it is inevitably necessary for a high-resolution transmission electron microscopic imaging that the specimen is sufficiently thin. Specimens for the transmission electron microscope are usually 30-100 nm, preferably 50-80 nm thick.

Specimens of this thickness can be obtained by cutting with the aid of an ultramicrotome, a sample embedded in polymer or a cryofixed sample (cryo-section) being cut into very thin sections. These so-called ultra-thin sections are then placed for microscopic examination on a carrier (also referred to as "grid") that is common in electron microscopy. The ultra-thin section technique has the disadvantage that it is very complex and difficult to be automated. On the other hand, it allows "looking into" the inner live of structures, e.g. of cells or organelles, which were cut through in the middle.

Another preparation method refers to the application of thin liquid films on an electron microscopic carrier. In the preparation of cryo-electron microscopic specimens a thin liquid film is frozen very rapidly while preventing the formation of ice crystals. To this end, an electron microscopic carrier ("grid") is immersed in a liquid containing the sample or the sample liquid is applied on the carrier by means of a pipette, the excess liquid is removed, for example, by means of a filter paper, and the liquid film remaining on the carrier is cryofixed by immersion in a bath of, for example, liquid ethane. In this context, the step of removing excess liquid, usually referred to as "blotting", is decisive for the quality and the reproducibility of the liquid film. For cryo-electron microscopy a thickness of the liquid film of about 70 nm is to be aimed at. Further, it is desirable when the grid is coated with the liquid film as uniform as possible and with reproducibility. In addition, it is desirable to produce a large amount of specimens with reproducibility. Since in cryo-electron microscopy, a contrasting agent is mostly dispensed with, the images obtained are noisy. Therefore, structure data have to be reconstructed by means of digital image processing. In addition, the cryofixed specimens show a higher sensitivity to the electron beam and are quickly damaged. For obtaining high-resolution images, usually many similar images of identical objects are averaged. Cryo-electron microscopy thus makes particularly high demands on the reproducibility of the specimen preparations.

From WO 02/077612 A1 (see also EP 1 370 846 B1 and US 0200401572184) a device of the type mentioned at the beginning is known with which "blotting" can be performed almost automatically. This device is commercially available under the trade name "Vitrobot". In this device, at first a carrier is fixed in a holder. After manual application of the sample liquid on the carrier, excess sample liquid is absorbed by means of one or two controllable blotting elements which can be moved towards the carrier ("blotting" operation). For the removing the liquid, a medium for absorbing liquid, e.g. a filter paper or another liquid-absorbing medium, is fixed on the blotting elements. The holder and the blotting elements are arranged in a humid environmental chamber in order to prevent drying out of the thin liquid film during the preparation. After blotting, the sample film is vitrified by immersion of the carrier in a cooling medium. Setting parameters comprise the number of blotting operations (a carrier can be blotted several times), the duration of the blotting, and the position of the carrier with respect to the filter paper. The device of WO 02/077612 A1 has the disadvantage that the blotting parameters are indeed reproducible, however the optimization requires long experimental series, e.g. when a sample liquid having a different viscosity is to be blotted. A further disadvantage is to be mentioned in connection with the described double-sided blotting mechanism. The carrier is squeezed by two filter paper disks on both sides with slight pressure. The pressure is dependent on the support for the filter paper, a foam rubber support, and can hardly be influenced. This can have a negative effect in particular for sensitive biological samples and coatings of the carrier grid and can result in mechanical damages to the objects to be microscopically examined or the delicate grid.

A semi-automated device similar to WO 02/077612 but having a simpler structure is commercially available under the trade name "Cryoplunge 3" by the company Gatan. Another device was described in the Article of S. Trachtenberg "A fast-freezing device with a retractable environmental chamber suitable for kinetic cryo-electron microscopy studies", Journal of Structural Biology 123:45-55 (1998). Other devices do not have automatic or motorized blotting mechanisms, as a result whereof a reproducible thickness of the liquid film cannot be achieved. Blotting is a manual operation and dependent on the skill of the user.

SUMMARY OF THE INVENTION

It is an object of the invention to remove the disadvantages known from the prior art and to provide an improved method or an improved device for performing the blotting operation, as a result whereof a reliable control and automation of this operation is made possible.

This object is solved by a device of the type mentioned at the beginning, in which, according to the invention, the device further has an optical sensor device comprising a light source and a receiver, and the optical sensor device is adapted to illuminate the absorbing medium by means of the light source and to detect a change in the optical properties of the absorbing medium by means of the receiver and to feed it to the control, and the control is adapted to move the blotting device away from the carrier given a change in the optical properties of the absorbing medium.

DETAILED DESCRIPTION OF THE INVENTION

The method on which the invention is based accordingly comprises the inventive steps of:
  detecting the change in the optical properties of the absorbing medium resulting from the absorption of the excess sample liquid into the absorbing medium by means of an optical sensor device which comprises a light source and a receiver, wherein the light source illuminates the absorbing medium and the receiver detects the change in the optical properties, and the change in the optical properties of the absorbing medium is fed to the control, as well as
  moving the blotting device away from the carrier based on the change in the optical properties of the absorbing medium detected by the optical sensor device and fed to the control.

Due to the inventive method or the inventive device the absorption of the excess sample liquid from the carrier ("blotting" operation) is automatically detected and a reliable signal for controlling and automating this operation is provided. A large number of specimens can be produced reproducibly. Compared to the device known from WO 02/077612 A1, no long experimental series for the optimization of the operation are necessary. A reproducible specimen preparation is considerably facilitated due to the invention.

The invention is particularly advantageous for the preparation of specimens which include biological material since biological material basically provides a bad contrast in the electron microscope, and the demands on reproducible specimens are thus particularly high.

The invention is suitable for all preparation methods in electron microscopy, in which the application of a liquid film of reproducible thickness on a carrier is provided. The invention is above all provided for the preparation of cryo-electron microscopic specimens since, here, particularly high demands on reproducible specimens are made.

The optical sensor device for detecting a change in the optical properties of the absorbing medium comprises a light source and a receiver, the light source illuminating the absorbing medium and the receiver detecting the optical properties of the absorbing medium. If the blotting device is moved towards the carrier and if the absorbing medium contacts the carrier, then the absorbing medium removes the excess liquid and absorbs it.

What is meant under the term "absorbing medium" is substantially a material which is capable of absorbing liquid and of changing the optical properties by the absorption of liquid. The absorbing medium can, for example, be a filter paper or another absorbent material, in which the liquid quickly spreads out and the absorbed liquid forms a wet area or "spot". In this wet area of the absorbing medium, the optical properties are changed. The change in the optical properties is preferably based on an abrupt increase or decrease in the transmission of light.

The change in the optical properties of the absorbing medium detected by the optical sensor device is fed to the control. After receipt of this signal, the control moves the blotting device away from the carrier, as a result whereof the blotting operation is terminated.

The term "carrier" refers to all carriers suited for electron microscopy, in particular to the already above-mentioned grids ("grid carrier"), the grids having differently formed holes (honey-combs, slits etc.) or a grid of defined mesh-number and/or can be coated with a film (e.g. coated grids of the company Quantifoil) and/or evaporated with carbon.

The holder is formed such that the usually very delicate and small grid (diameter of 2-3 mm) can be safely fixed. In a preferred version, the holder comprises a snap element having a first area for fixing the holder in the device and a second area for clamping a pair of tweezers having a very fine tip. The carrier is held by means of the pair of tweezers. The holder is formed such that it can be quickly mounted with reproducible accuracy on the device and again removed therefrom. The pair of tweezers clamped in the snap element can likewise be replaced. The holder is rotatably mounted about its longitudinal axis in order to allow blotting from the desired side of the grid. Further, the operator thus has the possibility to apply the sample liquid, which is usually manually applied with a pipette on the small grid, with the preferred hand.

The blotting device can be moved by a controllable drive, in particular a stepper motor drive. Thereby, the absorbing medium, which is arranged on the blotting device and is replaceable, is moved towards the carrier or again moved away from the carrier after detection of a change in its optical properties. Given a preferred realization, the absorbing medium is disk-shaped, e.g. a filter paper disk which is rotatably mounted on a ring located in the center of the disk. After each blotting operation, the disk is rotated further and can thus be used several times. For reasons of reproducibility, the absorbing medium is standardized, in particular with respect to its thickness and material quality. In a particularly preferred version, the absorbing medium is a filter paper of a specific type and quality. By the absorption of liquid during the blotting operation, a wet area having a higher light transmission is formed on the filter paper. As already mentioned above, according to the invention any liquid absorbing medium which changes its optical properties upon absorption of liquid is likewise suitable as an absorbing medium.

Depending on the sample liquid, it can be useful when between the detection of the change in the optical properties and the moving away of the blotting device from the carrier, the blotting device is still kept in its position for a predetermined amount of time. Here, the blotting device is not moved away from the carrier immediately after detection of the signal but still remains in its position for a predetermined amount of time. The blotting operation can thus be controlled even better and more individually.

The holder with the carrier as well as the blotting device are arranged in an environmental chamber in order to prevent the drying-out of the thin liquid film and thus the associated destruction of the examination objects.

For a reproducible blotting operation, it is advantageous in a preferred version when the absorbing medium is substantially planar, for example a filter paper, and when during the absorption of the sample liquid an area of the absorbing medium is oriented substantially parallel to the surface of the carrier.

In a particularly advantageous sub-version, the movement of the absorbing medium arranged on the blotting device towards the carrier is limited by a component of the holder serving as a stop. The component present on the holder can, for example, be the tip of a pair of tweezers holding the carrier. The stop, however, can likewise be formed by an element that is independent of the holder. When the absorbing medium located substantially parallel to the carrier surface comes even closer to the carrier, the stop allows for a deflection of the absorbing medium and thus for an adjustable angle between the absorbing medium and the carrier. The absorbing medium contacts the carrier on its edge, as a result whereof the liquid is removed via this side. This corresponds to the experiences of the manual removal of excess sample liquid. The manual removal of the liquid from the edge region of the carrier with a filter paper has proven to be particularly advantageous for producing reproducible and uniform liquid films.

Since the carrier covers a part of the absorbing medium, it is useful when the change in the optical properties of the absorbing medium is detected in an area which is located outside the area of the absorbing medium that is oriented substantially parallel to the carrier surface. Transmitter and receiver are directed onto an area of the absorbing medium which is usually wetted. The wet area or the spot arising during the removal of the liquid should consequently also be greater than the surface of the carrier. The size of the spot is inter alia also determined by the volume of sample liquid applied onto the carrier. In practice, it has shown that it is favorable for the practical realization when at least 3 µl, preferably 4-5 µl sample liquid are applied on the carrier.

With respect to the arrangement of the transmitter and the receiver of the optical sensor device, in an advantageous version the substantially planar absorbing medium is arranged between the light source and the receiver. Given this version, the optical sensor device can be formed in the form of a light barrier, the optical axis of which extends transversely through the absorbing medium in an area which is wetted by the absorption. For example, the absorption of liquid by a filter paper can result in an abrupt increase in the transmission of light at the wet spot. The change in the transmission is detected by the light barrier.

It is useful for the setting of the optical sensor device and for the detection when the optical sensor device is arranged on the blotting device. The optical sensor device is moved together with the blotting device when the blotting device is moved towards the carrier for absorption of the sample liquid or is moved away from the carrier.

It is also possible to arrange the optical sensor device on the chamber wall. The optical sensor device is then not moved together with the blotting device. However, this realization has the disadvantage that the distance between the transmitter and the receiver is greater and the signal can thus be worse than given a sensor device arranged on the blotting device.

Due to the scattering effect of the light at the absorbing medium, it is not inevitably necessary that transmitter and receiver of the light barrier lie in one line. The beams of the transmitter and receiver shall however meet on the absorbing medium and enclose an angle of preferably less than 30° with respect to the optical axis.

If the inventive device is used for the preparation of cryo-electron microscopic specimens, then the device further has a cooling device for cooling down the carrier wetted with the sample liquid. The carrier is cooled down in a cooling device after absorption of the excess sample liquid and the moving away of the blotting device. As described above, this operation has to take place very quickly in order to prevent the formation of ice crystals which destruct the structure of the examination objects. The sample liquid is vitrified, i.e. it solidifies in a glass-like condition. Usefully, the sample liquid present on the carrier is vitrified by immersion of the carrier in a cooling medium. Preferably, liquid ethane is used as a cooling medium. Since after generating the thin liquid film on the carrier, each contact of the carrier with the outer surrounding is to be avoided, the carrier is directly conveyed from the environmental chamber into the cooling medium. The cooling device can, for example, be arranged directly underneath the environmental chamber. After the blotting operation, an opening in the chamber floor is cleared and the carrier is lowered into a cryogen container located underneath.

In the following, the invention along with further advantages is explained with reference to a non-restrictive embodiment which is illustrated in the enclosed drawings.

DETAILED DESCRIPTION OF THE DRAWINGS

Figure 1:
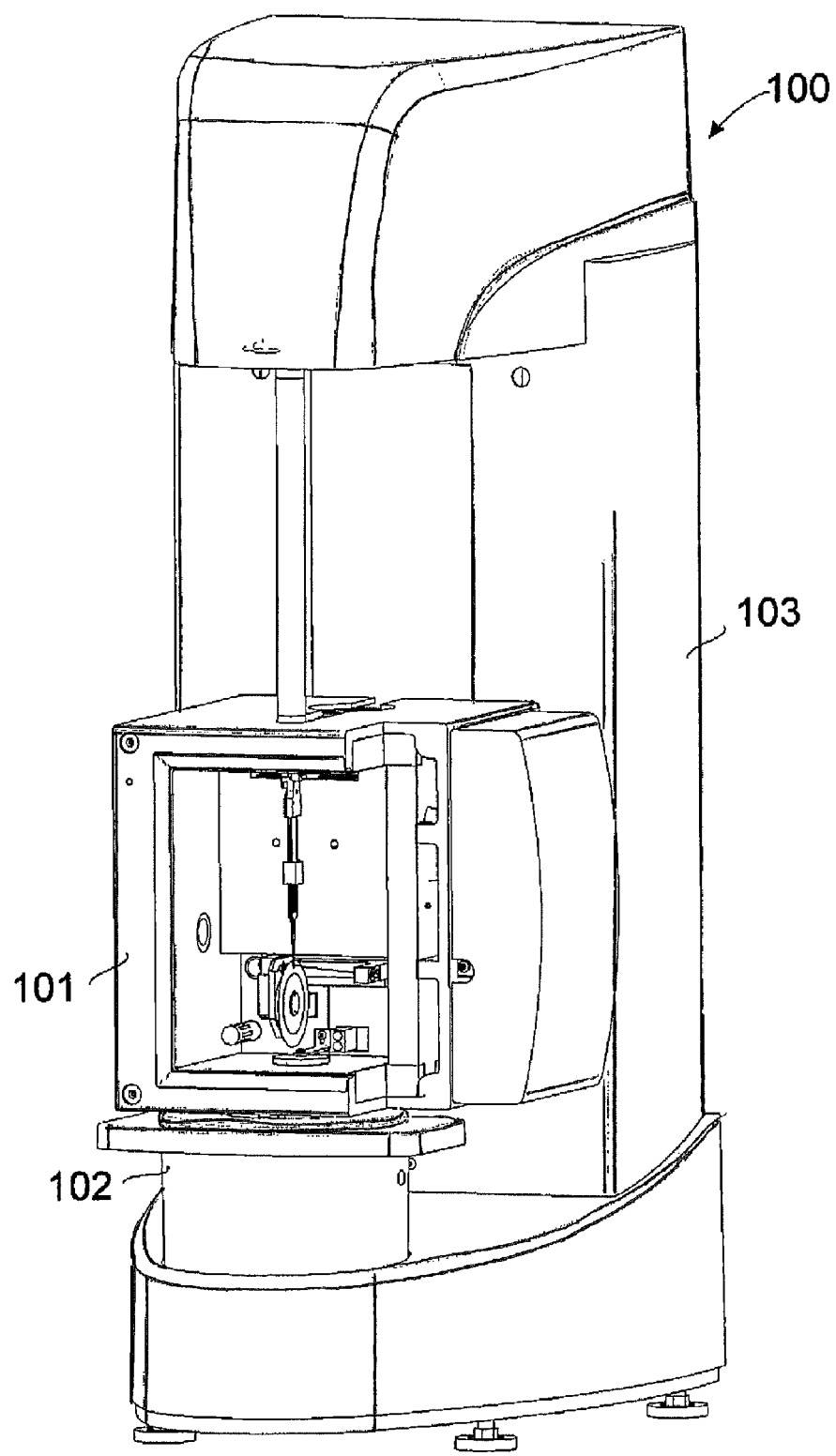
FIG. 1 shows the specimen preparation system according to the embodiment in an oblique view.

FIG. 1 shows in an oblique view a device 100 for preparing specimens for a cryo-electron microscope. The device 100 comprises as essential components a preparation environmental chamber 101 and a cooling device 102. The cooling device 102, in which a container with a cryogen is located, is arranged immediately underneath the preparation chamber 101. The container with the cryogen can be removed from the device so that the vitrified specimen can be transferred into the electron microscope. In the boarded rear part 103 of the device 100, various stepper motors as well as a control is housed, which are not illustrated in more detail here.

Figure 2:
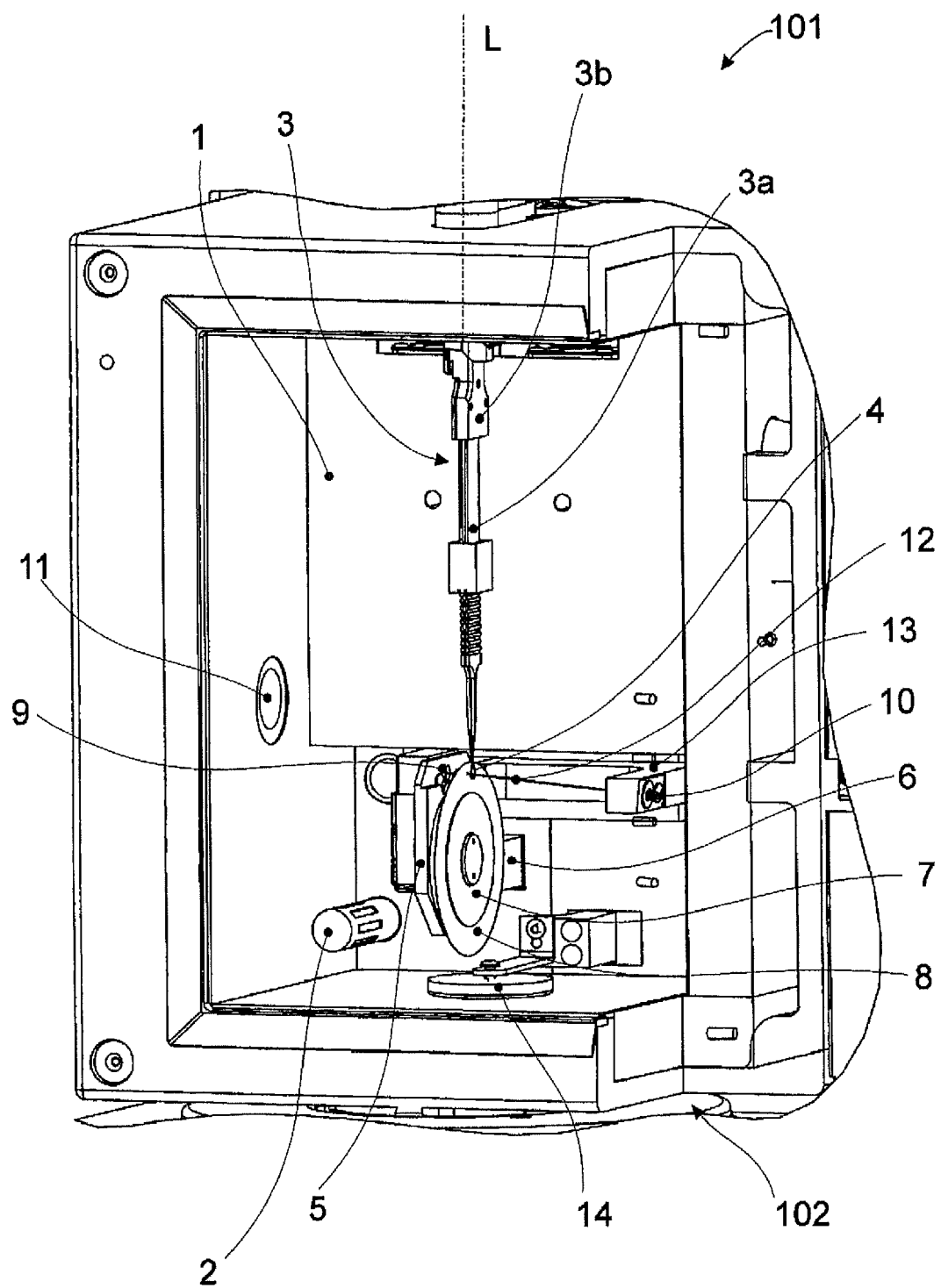
FIG. 2 shows an enlarged view of the open preparation chamber from FIG. 1.

FIG. 2 shows an enlarged view of the open preparation chamber from FIG. 1. The preparation chamber is an environmental chamber. For temperature setting, heating and cooling elements 1 are arranged on the rear side of the chamber. By means of a piezo nozzle, arranged laterally outside of the chamber 101 and not illustrated in FIG. 2, the air humidity in the chamber 101 can be increased via a tube connection. The air humidity and the temperature are controlled via a sensor 2. In the preparation chamber 101 there is further a holder 3 for a carrier grid 4. In this embodiment, the holder 3 is designed in the two-part form and comprises a pair of tweezers 3a for fixing the carrier grid 4 as well as a snap element 3b which, on the one hand, accommodates the pair of tweezers 3a and, on the other hand, fixes the holder 3 in the device. So that the operator can comfortably clamp the carrier grid 4 with the pair of tweezers 3a outside of the preparation chamber in the pair of tweezers, the entire grid holder 3 can be mounted and again removed quickly and with reproducible accuracy on/from the device. As needed, the pair of tweezers 3a can likewise be simply replaced. The holder 3 can be rotated by 180° in both directions about its longitudinal axis L.

The sample liquid is applied manually onto the carrier grid 4 by means of a pipette. For this, the preparation chamber 100 has a preferably laterally arranged opening 11 for insertion of the pipette on a level with the carrier grid 4. The applied liquid volume usually amounts to 4-5 μl.

For absorbing the excess liquid, a blotting device 5 is provided in the preparation chamber 101 which blotting device can be moved towards the carrier grid 4 and again away from the carrier grid by means of a stepper motor drive housed in the back part 103 (see FIG. 1) and not illustrated here. The movement of the blotting device 5 is controlled by means of a control. In the illustrated embodiment, the blotting device is pivotably mounted, namely about an axis parallel to the longitudinal axis L of the holder 3. The blotting device 5 is comprised of a pivot arm 6 on which a mounting ring 7 for a disk-shaped filter paper 8 is mounted. When the blotting device 5 is moved towards the carrier grid 4, then the filter paper 8 eventually contacts the carrier grid 4 almost parallel, and the excess liquid on the carrier grid 4 is removed from the carrier surface with the filter paper 8 serving as an absorbing medium. What remains is a thin liquid film having a thickness of about 70 nm. The absorption of the excess liquid is also referred to as "blotting".

For monitoring the blotting operation, an optical sensor device in the form of a light barrier 12 is provided in the preparation chamber 101. The light barrier which is realized with the aid of a light source 9 and a receiver 10, is illustrated by a connecting beam 12. In the illustrated embodiment, the light source 9 and the receiver 10 are arranged on the blotting device 5 and are moved together with the blotting device 5 when the blotting device is moved. The receiver 10 is arranged on an extension arm 13. An exchange of the light source 9 and of the receiver 10 has no effect on the detection. Due to the scattering effect of the light on the filter paper, it is not necessary either that the light source 9 and the receiver 10 of the light barrier lie in one line. The beams of the light source 9 and of the receiver 10 should however meet at the filter paper 8 and enclose an angle of preferably less than 30° with respect to the optical axis. In practice, the one-way light barriers MICROmote® DLM30R (type of light: red 660 nm; nominal range: 300 mm) or DLM30L (type of light: infrared 880 nm; nominal range: 800 mm) of the company STM have proven particularly favorable because they allow for a very high range given a very small construction. The MICROmote® one-way light barriers are operated with a separate switching amplifier (V8-A, V8-B or V8-F) which has an automatic as well as a manual mode for setting the sensitivity.

After the blotting operation, an opening in the chamber floor is cleared by a flap 14, and the carrier grid 4 is lowered very fast by vertical movement of the holder 3 into the cryogen container of the cooling device 102 located underneath the chamber, as a result whereof the liquid film present on the carrier grid 4 is vitrified.

Figure 3:
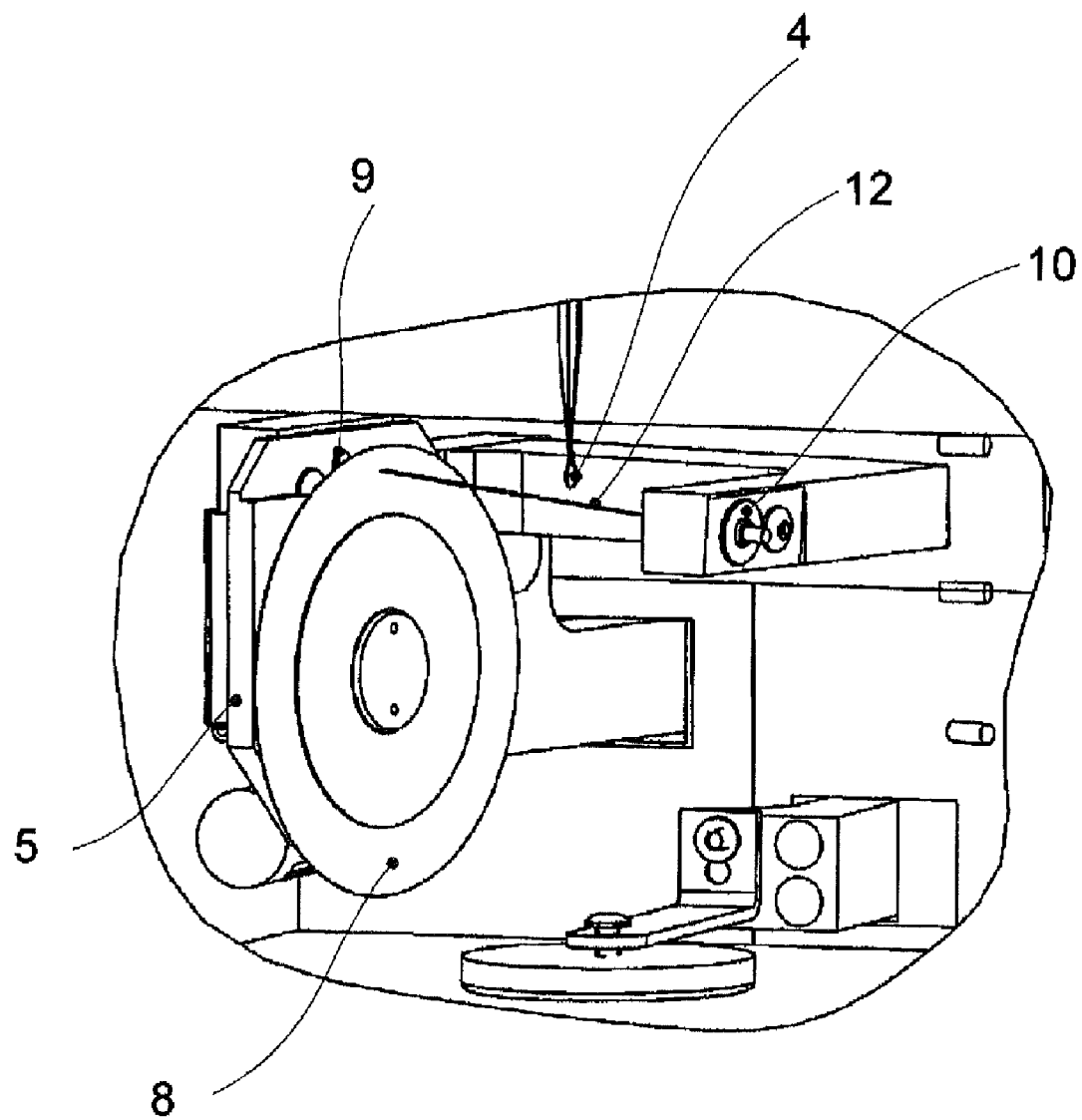
FIG. 3 shows a further enlarged view of the preparation chamber from FIG. 1, in which the blotting device is directed away from the carrier.
Figure 4:
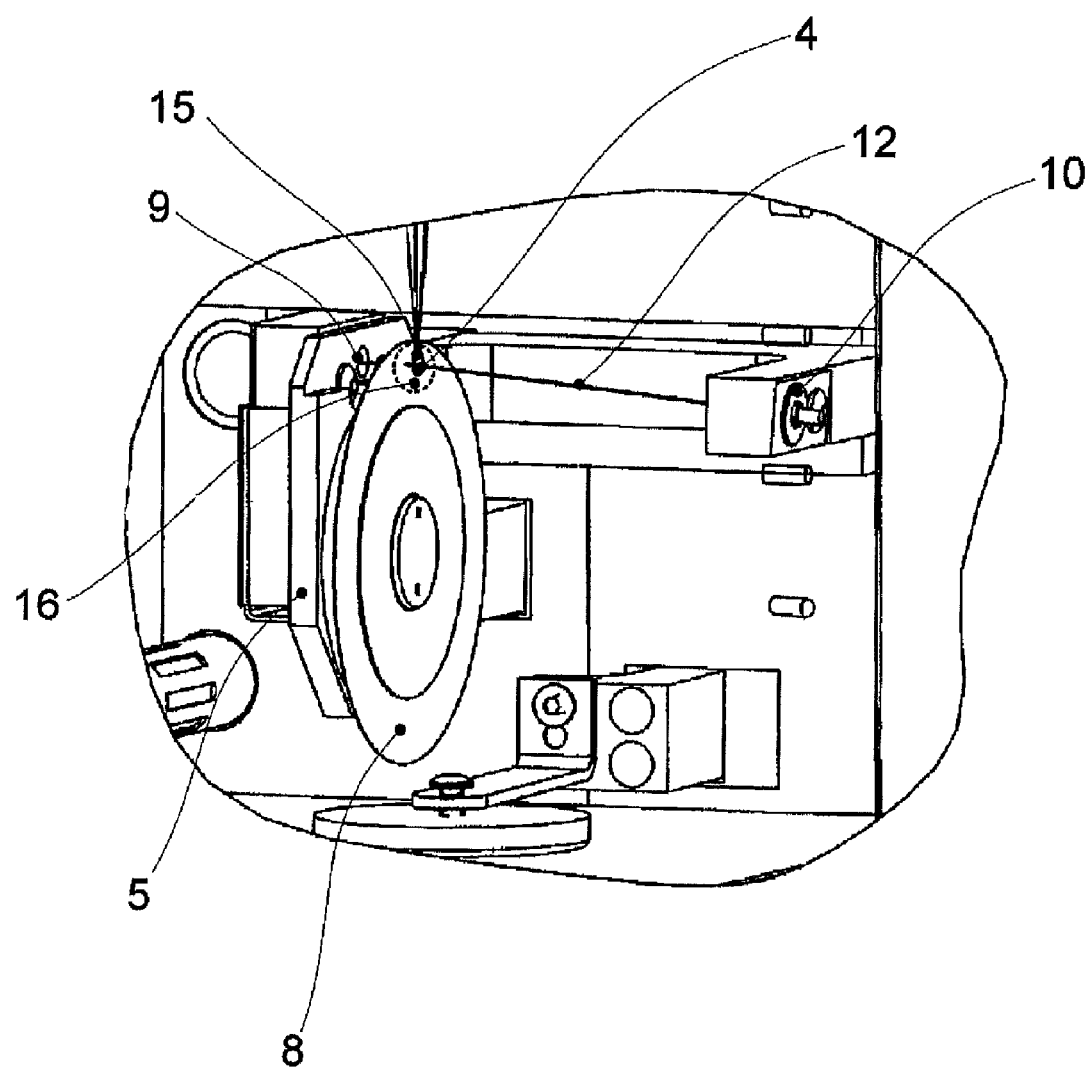
FIG. 4 shows the further enlarged view of the preparation chamber from FIG. 1, with the blotting device moved towards the carrier.

The blotting operation is still explained in more detail with reference to FIGS. 3 to 5:

FIG. 3 is a further enlarged view of the preparation chamber from FIG. 1, in which the blotting device 5 is directed away from the carrier grid 4. This is the initial state. In this state, the sample liquid is applied on the carrier grid 4 by means of a pipette as described above in FIG. 2. At the grid 4, a liquid meniscus is formed thereby. The light barrier 12 with the light source 9 and the receiver 10 is again illustrated with a connecting beam 12.

In the next step, the blotting device 5 is approached towards the carrier grid at a defined speed, at first a little faster and then slowly, until the switching point of the sensor device, i.e. the point at which the receiver 10 detects a signal, is reached. The approach is stopped. The light source 9 and the receiver 10 are both mounted on the blotting device 5 and are moved therewith. This state is illustrated in FIG. 4. The filter paper 8 is now oriented substantially parallel to the surface of the carrier grid 4. By means of the pipette tip 15 which serves as a stop for the filter paper 8, the filter paper 8, which rests on the pipette tip 15 with little pressure, is deflected, and an angle is formed between the filter paper 8 and the carrier grid 4 which can be set via the bearing pressure. The filter paper 8 contacts the carrier grid 4 on its edge opposite to the pipette tip 15. When the filter paper 8 contacts the carrier grid 4 and absorbs the excess liquid, the liquid spreads out quickly in the filter paper 8 and a wet area 16 (illustrated by the broken line) or a spot is formed around the carrier grid 4. At this wet spot, the transmission of light abruptly changes, normally it increases. This abrupt change in the transmission is detected in the receiver 10 of the light barrier 12 as a signal, and the signal is fed to the control (not illustrated) via a signal connection. In doing so, it is useful when the spot is greater than the grid 4 since the grid 4 covers a part of the filter paper 8. Accordingly, the jump in light intensity is detected in an area which is located outside the carrier grid surface. The light source 9 and the receiver 10 are thus directed onto an area of the filter paper 8, which is usually wetted but is located outside of the area of the filter paper 8 covered by the carrier grid 4.

The next step, the "holding time" is optional and dependent on the respective sample. The holding time indicates how long the contact between the filter paper 8 and the carrier grid 4 is maintained after the switching point of the sensor device has been reached. During the holding time, the position of the blotting device 5 is not changed. The holding time can be set in advance independent of the sensor device in the control.

As soon as the switching point of the sensor device is reached or the holding time is over, the control provides the signal to the stepper motors to move the blotting device 5 again away from the carrier grid 4 into its initial position, as illustrated in FIG. 3.

The carrier grid 4 which is now covered with a thin sample film is then lowered through an opening in the floor of the preparation chamber 101 into the cryogen, preferably liquid ethane.

In the end, the disk-shaped filter paper 8 is rotated further by a distance by means of a controlled rotary mechanism in the mounting ring 7 so that an unwetted area on the filter paper 8 is provided for the next blotting operation.

Figure 5:
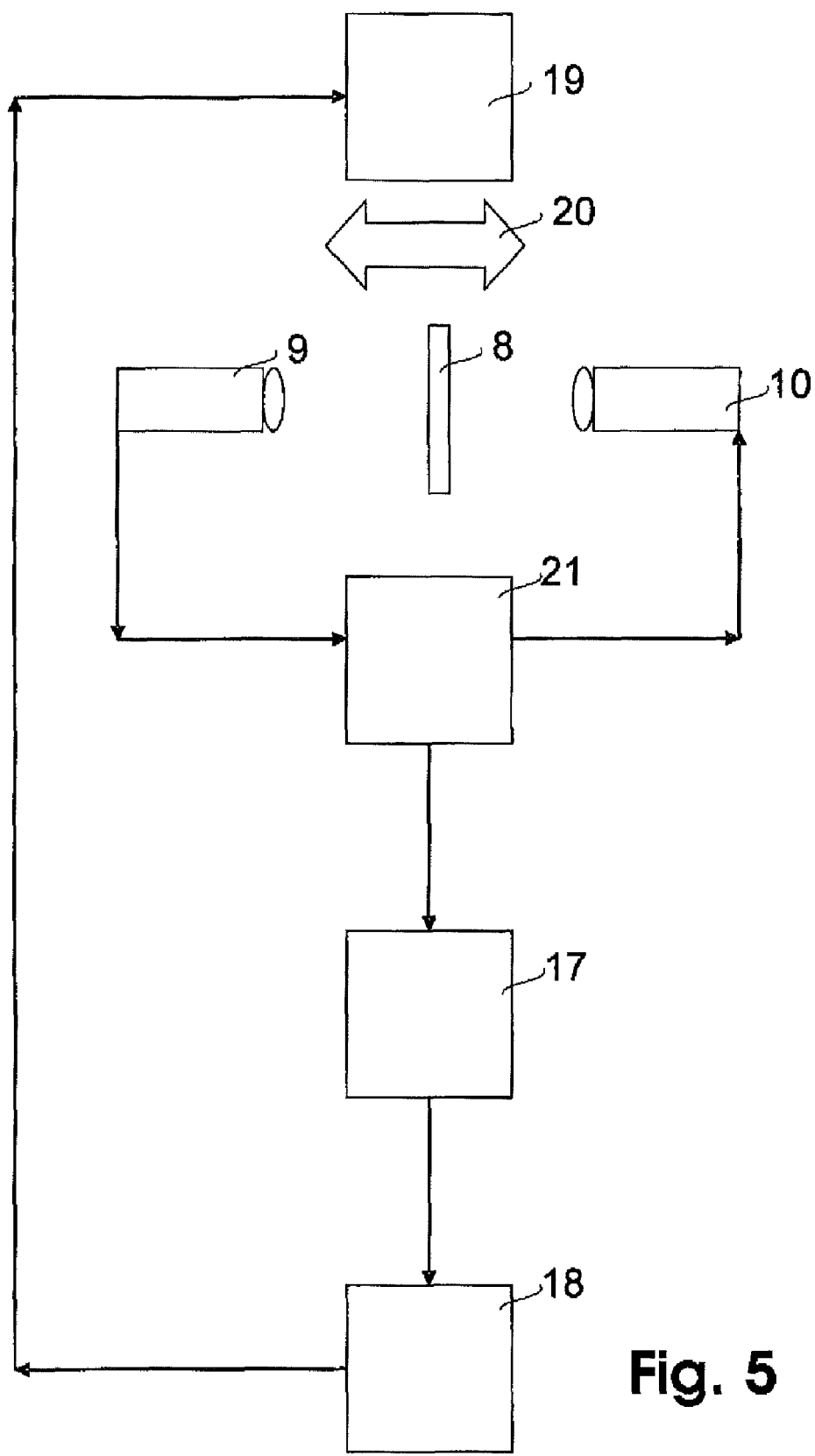
FIG. 5 shows a block diagram of the closed loop circuit of the blotting operation.

In FIG. 5, the closed loop control of the blotting operation is illustrated once again in a block diagram. The movement of the blotting device 5 on which the filter paper 8 is arranged, takes place by means of a stepper motor 19. The stepper motor 19 is controlled via a stepper motor driver 18 by the control 17. By the movement of the blotting device 5, the filter paper 8 is moved towards or away from the carrier grid 4 (not illustrated). The directions of movement of the filter paper 8 or, respectively, of the blotting device 5 are symbolized by the double arrow 20. The filter paper 8 is arranged between the light source 9 and the receiver 10. The light source 9 and the receiver 10 are connected to a control 17 via a switching amplifier 21. During blotting, the blotting device 5 is moved towards the carrier grid 4 by means of the controlled stepper motor 19, and the filter paper 8 absorbs the excess sample liquid from the carrier grid 4. If now a change in the light transmission of the filter paper 8 is detected by the receiver 10, then this is forwarded to the control 17. The control 17 processes this as described above and outputs the signal to the stepper motor to move the blotting device 5 and thus the filter paper 8 again away from the carrier grid 4.

In practice, a calibration of the device with a defined liquid amount and water (or possibly another solution) is performed once before the beginning of operation, and the optical sensor device is adapted to the size of the formed wet area on the filter paper. The major part of the samples is aqueous and with respect to the blotting behavior can be equated to the one of water. After calibration of the device, the operator merely has to stick to the defined liquid amount. This is a great advantage over the above-mentioned device of WO 02/077612 A1 (Vitrobot) which requires complex experimental series. Exceptions with regard thereto are industrial samples, such as lacquers, for which the device would have to be re-calibrated. For this application, the automatic mechanism with the sensor can also be dispensed with and the blotting device can merely be controlled to an end position. In an adjustment mode provided in the device, this end position can be set very precisely under visual observation and stored. The end position is then reproducible for all further samples and does not require long experimental series. This, too, offers an advantage over the Vitrobot which, during double-sided blotting, presses the two filter papers against the carrier grid by means of a foam support without positioning accuracy.

The above-described realization is only one example among many and consequently is not to be considered as being restrictive.

What is claimed is:

1. An automated method for preparing cryofixed specimens embedded in a sample liquid for a cryo-electron microscope, comprising:
    fixing a carrier to a holder that is located in an environmental chamber,
    applying a sample liquid on the carrier for wetting the surface of the carrier with sample liquid,
    automatically moving a blotting device by a motor driven mechanism for absorbing the sample liquid by an absorbing medium towards the carrier by means of a closed-loop control,
    removing excess sample liquid present on the carrier by means of the absorbing medium arranged on the blotting device and absorbing the sample liquid into the absorbing medium,
    illuminating the absorbing medium by means of a light source,
    detecting the change in the optical properties of the absorbing medium resulting from the absorption of the excess sample liquid into the absorbing medium by means of an optical sensor device having a receiver,
    feeding the change in the optical properties of the absorbing medium as a controlling parameter to the closed-loop control,
    moving away the blotting device by a motor driven mechanism from the carrier controlled by the change in the optical properties of the absorbing medium detected by the sensor device and fed to the control that controls the motor driven mechanism.

2. The method according to claim 1, further comprising providing an absorbing medium that is substantially planar and, orienting an area of the absorbing medium during absorption of the sample liquid substantially parallel to the surface of the carrier.

3. The method according to claim 2, further comprising limiting of the movement of the absorbing medium arranged on the blotting device towards the carrier by a component of the holder serving as a stop.

4. The method according to claim 2, further comprising detecting of the change in the optical properties of the absorbing medium in an area that is located outside of the area of the absorbing medium and is oriented substantially parallel to the carrier surface.

5. The method according to claim 4, further comprising applying at least 3 µl sample liquid to the carrier.

6. The method according to claim 1, further comprising still maintaining the blotting device in its position for a predetermined amount of time between detecting the change in the optical properties of the absorbing medium and moving away of the blotting device from the carrier.

7. The method according to claim 1, further comprising cooling the carrier wetted with sample liquid in a cooling device after the excess sample liquid has been absorbed and the blotting device has been moved away.

8. The method according to claim 7, further comprising vitrifying the sample liquid present on the carrier by immersing the carrier in a cooling medium.

9. The method according to claim 7, further comprising providing liquid ethane as a cooling medium.

10. The method according to claim 1, further comprising providing the method for a cryo-electron microscope.

11. A device for automatically preparing cryofixed specimens for a cryo-electron microscope, the specimens being embedded in a sample liquid, said device comprising:
    a holder for holding a carrier,
    a movable blotting device that is movable by a motor driven mechanism for absorbing excess sample liquid applied on the carrier by means of a substantially planar absorbing medium,
    a closed-loop control that is adapted to provide a signal to the motor driven mechanism to move the blotting device towards the carrier,
    an environmental chamber in which the holder and the blotting device are arranged,
    an optical sensor device comprising a light source and a receiver, wherein the optical sensor device is adapted to illuminate the absorbing medium by means of the light source and to detect a change in the optical properties of the absorbing medium by the receiver and to feed the change as a controlling parameter to the closed-loop control, and the closed-loop control is adapted to provide a signal to the motor driven mechanism to move the blotting device away from the carrier depending on a change in the optical properties of the absorbing medium as a controlling parameter.

12. The device according to claim 11, further comprising a cooling device for cooling down the carrier wetted with sample liquid.

13. The device according to claim 11, wherein the substantially planar absorbing medium is arranged between the light source and the receiver of the optical sensor device.

14. The device according to claim 13, wherein the beam of the light source and an optical axis of the receiver meet on the absorbing medium and enclose an angle of less than 30°.

15. The device according to claim 11, wherein the optical sensor device is arranged on the blotting device.

16. The device according to claim 11, wherein the electron microscope is a cryo-electron microscope.

\* \* \* \* \*